United States Patent [19]

Nielsen et al.

[11] Patent Number: 5,569,671

[45] Date of Patent: Oct. 29, 1996

[54] FUNGICIDALLY ACTIVE COMPOUNDS

[75] Inventors: Ruby I. Nielsen, Farum; Frank W. Rasmussen, Valby, both of Denmark

[73] Assignee: Novo Nordisk A/S, Bagsvaerd, Denmark

[21] Appl. No.: 427,012

[22] Filed: Apr. 24, 1995

Related U.S. Application Data

[60] Division of Ser. No. 95,785, Jul. 22, 1993, Pat. No. 5,409,951, which is a continuation-in-part of Ser. No. 714,107, Jun. 11, 1991, abandoned.

[30] Foreign Application Priority Data

Jun. 15, 1990 [DK]  Denmark ................................. 1461/90

[51] Int. Cl.⁶ ..................... A01N 43/16; A01N 57/00; A61K 31/35; A61K 31/675
[52] U.S. Cl. ................... 514/455; 514/63; 514/80; 514/140; 514/147; 514/231.2; 514/239.5; 514/317; 514/383; 514/388; 514/399; 514/433; 514/471
[58] Field of Search ..................... 514/455, 399, 514/383, 63, 239.5, 231.2, 317, 388, 433, 471, 80, 147, 140

[56] References Cited

U.S. PATENT DOCUMENTS

| | | | |
|---|---|---|---|
| 3,873,529 | 3/1975 | Sasaki et al. | 260/240 R |
| 4,070,458 | 1/1978 | Umezawa et al. | 424/177 |
| 4,500,544 | 2/1985 | Hosokawa et al. | 514/543 |
| 4,915,724 | 4/1990 | Watson et al. | 71/65 |

OTHER PUBLICATIONS

Hooper et al. J. Chem. Soc., vol. 11, pp. 3580–3590 (1971).
Kurobane et al, Tetrahedron Letters, vol. 47, pp. 4633–4666 (1978).
Franck et al., Chemiche Berichte, vol. 99, No. 12, pp. 3842–3862 (1966).

*Primary Examiner*—Allen J. Robinson
*Attorney, Agent, or Firm*—Steve T. Zelson, Esq.; Cheryl H. Agris, Esq.

[57] ABSTRACT

Novel compounds of formula I

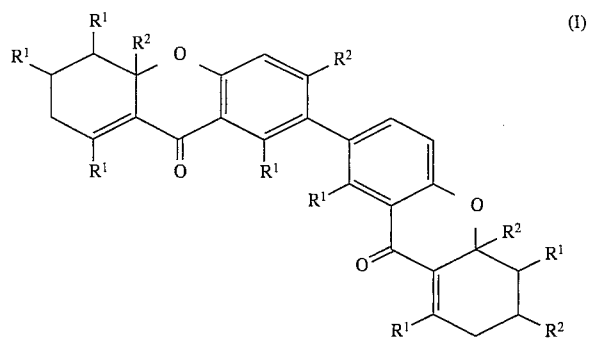

wherein $R^1$ is independently hydrogen, hydroxy, alkyl with 1 to 6 carbon atoms, acyloxy groups with 1 to 6 carbon atoms, alkyloxy with 1 to 6 carbon atoms or from 1 to 5 sugar moieties; and $R^2$ is independently hydrogen, or alkyl with 1 to 6 carbon atoms.

The compounds are producible by aerobic cultivation on suitable nutrient media under suitable conditions of a strain of the fungus Ascochyta sp., subsequent recovery of the active component from the fermentation medium, and optionally modifying the active compound to obtain a compound of the desired formula I.

Disclosed is also microorganisms capable of producing said compounds, compositions containing said compounds, and the use of such compositions for controlling fungi in valuable crops, animals, including birds and mammals, and in the preservation of wood, paints and edible products.

18 Claims, 2 Drawing Sheets

FUNGICIDALLY ACTIVE COMPOUNDS

This application is a divisional application of application Ser. No. 08/095,785, filed Jul. 22, 1993, now U.S. Pat. No. 5,409,951, issued Apr. 25, 1995, which is a continuation-in-part U.S. application Ser. No. 07/714,107, filed Jun. 11, 1991, now abandoned.

FIELD OF THE INVENTION

This invention relates to novel fungicidally active compounds, methods of producing such compounds, microorganisms capable of producing said compounds, compositions containing said compounds, and the use of such compositions for controlling fungi in valuable crops, animals, including birds and mammals, and in the preservation of wood, paints and edible products.

BACKGROUND OF THE INVENTION

For a number of years it has been known that various microorganisms produce metabolites exhibiting biological activity so as to be useful as biocides for combating diseases and pests.

Especially it has been known that some species of the genus Ascochyta produce different metabolites exhibiting biological activity, in particular as phytotoxins.

Examples thereof are e.g. an isoquinoline alkaloid, chrysantone, isolated from *Ascochyta chrysanthemi* (*Phytochemistry*, 28(3): 923–927, 1989), which is a phytotoxin, and which also exhibits an inhibitory effect on the growth of *Bacillus cereus, B. subtilis, Escherichia coli* and a weak antifungal activity on *Cladosporium cucumerinum*.

Chrysantone was found to have the formula (a) below:

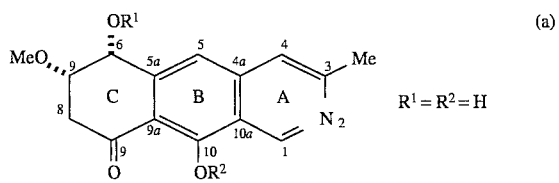

Ascotoxin (Decumbin) produced by A. imperfecta (Y. Suzuki, H. Tanake, H. Aoki and T. Tamura, *Agric. Biol. Chem.* 1970, 34, 395), is a strong plant pathogen with a phytotoxic activity exhibiting a strong inhibition of the growth of lucerne and rape. The isolated compound has the formula (b) below:

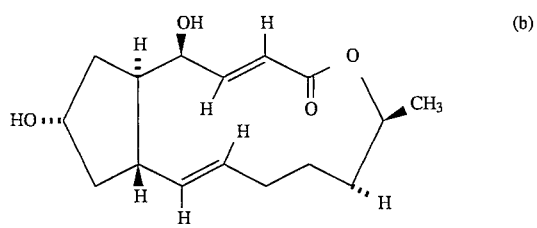

Cytochalasin A and B produced by A. heteromorpha (*J. Natural Products*, 50 (5): 989–998, 1987) are well known myco- and phytotoxins belonging to the cytochalasins a class of mold metabolites exhibiting various effects. The cytochalasins are all characterized by a highly substituted isoindole ring to which is fused a macrocyclic ring. An example is cytochalasin B of formula (c) below:

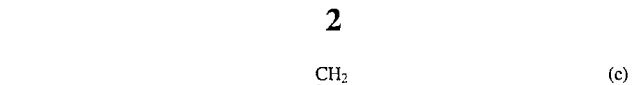
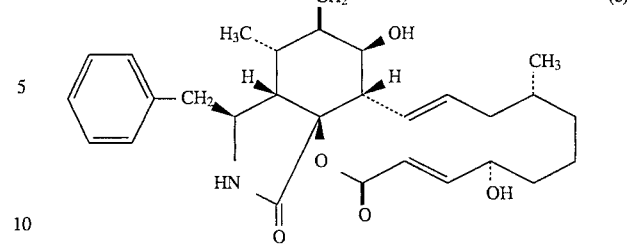

Solanopyrones A and C, two well known phytotoxins of formula (d) and (e), respectively, have been isolated from *A. rabiei* (*Phytochem.*, 28: (10) 2627–2630, 1989)

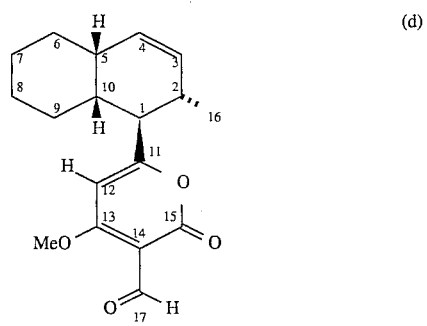

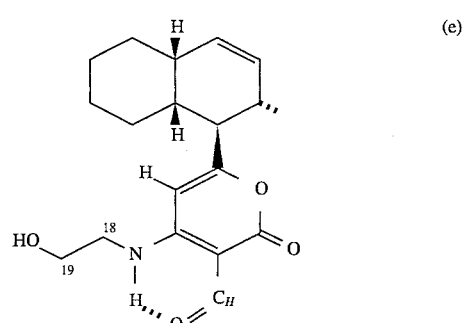

These compounds are not useful for combating plant diseases and pests because they are strong phytotoxins.

Although progress has been made in the field of identifying and developing biological biocides for combating various diseases and pests in plants and animals of agronomical importance, most of the biocides in use are still synthetic compounds that are difficult to decompose in nature and have a broad spectrum of activity.

In the last decade or so there has been a still increasing concern for the impact of such biocides on the environment and the ecosystems surrounding farmlands, and consequently there exists an outspoken need for biocides that are more specific in their activity, and are readily degradable in the natural environment.

SUMMARY OF THE INVENTION

As indicated above known metabolites from the mold genus Ascochyta, all have exhibited a strong phytotoxic activity, but it has now surprisingly been found that fungi belonging to said genus also produce metabolites that exhibit strong antifungal activity, and that are substantially without phytotoxic activity.

The present invention in its first aspect concerns novel compounds of the general formula I, wherein the substituents $R^1$, and $R^2$, have the meanings indicated below.

In its second aspect the invention relates to processes used for the production of the novel compounds of formula I.

These processes comprise use of specific microorganisms as well as chemical processes for full and/or semi synthetic production of said compounds.

In a third aspect of the invention it relates to fungicidal compositions comprising the novel compounds of formula I in combination with suitable excipients, such as diluents, carriers, etc.

Within the context of the invention it is also contemplated to combine the novel compounds of formula I with known biocides for making up novel combination compositions.

Furthermore the invention in a fourth aspect relates to methods of combating plant diseases by application of compositions comprising the novel compounds of formula I to infested areas.

In a fifth aspect the invention relates to the use of the novel compounds of formula I for combating or controlling plant diseases, especially fungal attack.

The invention further relates to a biologically pure culture having all of the identifying characteristics of a strain of Ascochyta sp. deposited with the Commonwealth Mycological Institute Culture Collection and assigned accession no. CMI CC No. 337158.

DEPOSIT OF MICROORGANISMS

For the purpose of describing this invention in detail a strain of the fungus Ascochyta sp. (CMI CC No. 337158) has been deposited with the Commonwealth Mycological Institute Culture Collection (CMI CC), Ferry Lane, Kew, Surrey TW9 3AF, England, for the purposes of patent procedure on the date indicated below. CMI CC being an international depository under the Budapest Treaty affords permanence of the deposit in accordance with rule 9 of said treaty.

| Deposit date | 6 February 1990 |
|---|---|
| Depositors ref. | 33 429 |
| CMI CC designation | CMI CC No. 337158 |

CMI CC 337158 belongs to the class Deuteromycetes, sub-class Coelomycetidae, and family Sphaerioidaceae. The fungus is a new species of the genus Ascochyta which was isolated in 1988 from a leaf of *Panicum maximum*.

BRIEF DESCRIPTION OF THE DRAWING

The invention is described in further detail below with reference to the drawings, wherein.

DETAILED DESCRIPTION OF THE INVENTION

Figure 1:
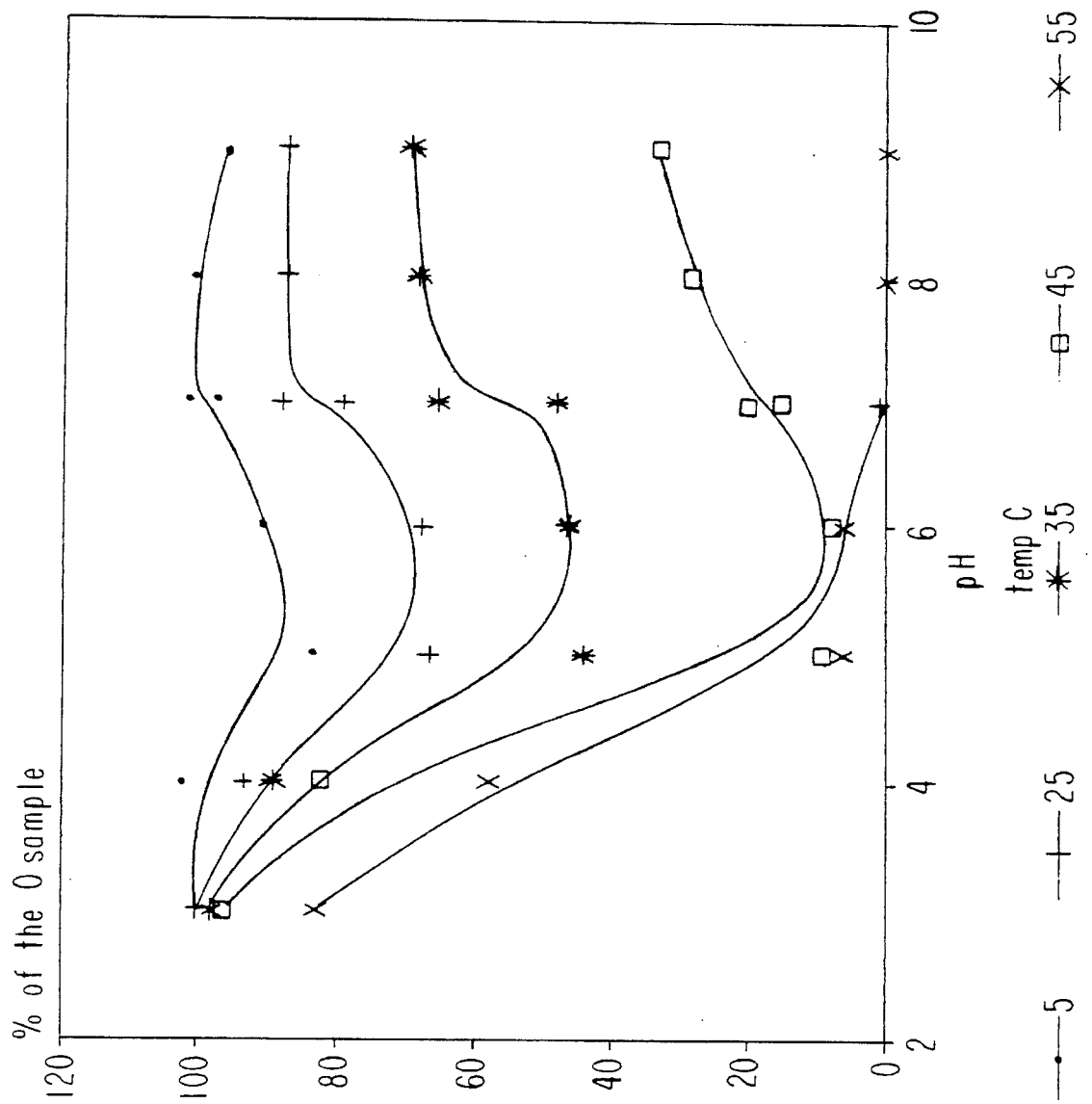
FIG. 1 shows a graphical representation of the stability/ activity relationship with temperature and pH for a novel compound according to the invention.

As indicated above the invention relates in its first aspect to novel compounds of formula I

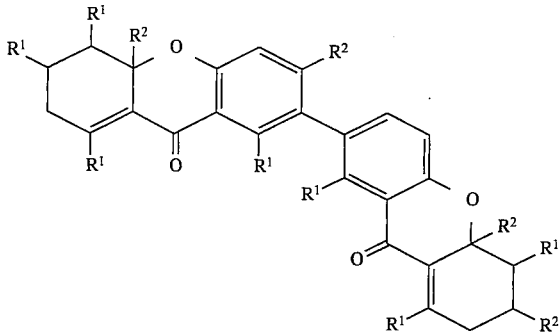

wherein $R^1$ is independently hydrogen, hydroxy, alkyl with 1 to 6 carbon atoms, acyloxy groups with 1 to 6 carbon atoms, alkyloxy with 1 to 6 carbon atoms, or from 1 to 5 sugar moieties; and $R^2$ is independently hydrogen, or alkyl with 1 to 6 carbon atoms.

In a specific embodiment, the invention relates to a compound (Ia) of formula I, wherein $R^1$ is —OH, and $R^2$ is —$CH_3$.

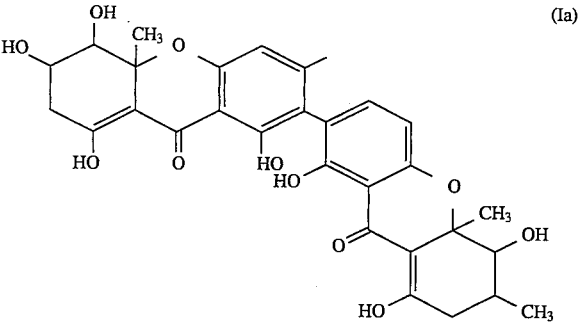

In a most specific embodiment, compound Ia has the stereoconfiguration of

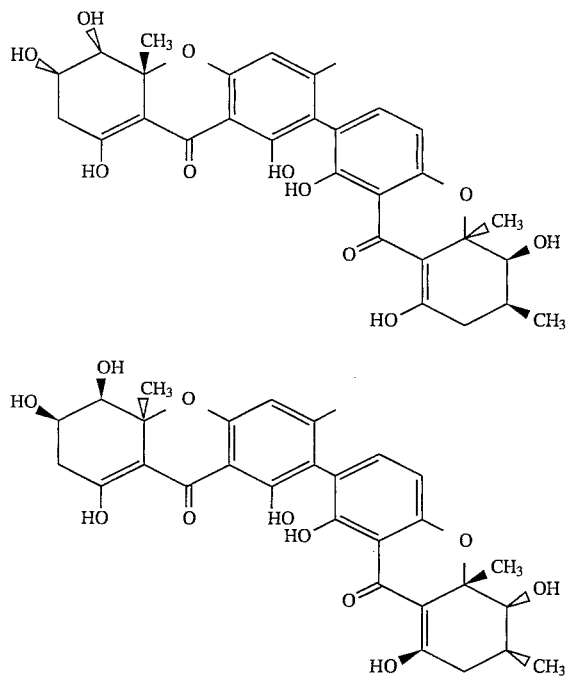

Compounds of this class of organic structures with formula I are novel. It has not been possible to identify references in the literature to such structures.

The compound of formula Ia may be isolated as a metabolite from a novel species of the genus Ascochyta, Ascochyta sp. (CMI CC No. 337158).

According to its second aspect the invention relates to processes for the production of the novel compounds of formula I.

In a specific embodiment, the compound of formula Ia may be prepared by aerobic cultivation on suitable nutrient media under conditions hereinafter described with a strain of the fungus Ascochyta sp. (CMI CC 337158) and thereafter recovering the active component from the fermentation medium.

The natural metabolite may subsequently be modified chemically in order to obtain various derivatives thereof. The derivatives may be produced in order to improve certain properties with the metabolite such as its solubility in aqueous media, its hydrophobicity, hydrophilicity, stability, specificity, etc. It is also contemplated that compounds according to the invention may be produced by well known chemical synthetic processes using available starting materials.

One group of derivatives is compounds of formula I or in a specific embodiment, Ia, wherein one or several hydroxy groups have been glycosylated.

Another group comprises compounds of formula I or in a specific embodiment, Ia, wherein one or several hydroxy groups have been acylated.

A further group of derivatives is compounds of formula I or in a specific embodiment, Ia, wherein one or several hydroxy groups have been alkylated.

Although the invention discussed herein below, principally deals with the specific strain CMI CC 337158, it is well known in the art that the properties of microorganisms may be varied naturally and artificially. Thus all strains of Ascochyta sp. including variants, recombinants and mutants, whether obtained by natural selection, produced by the action of mutating agents such as ionizing radiation or ultraviolet irradiation, or by the action of chemical mutagens such as nitrosoguanidine, are included in this invention.

It is also well known that closely related fungal species within a genus produce related metabolites of the same or similar activity, but with slight differences in chemical structure. The present invention therefore is meant to encompass such closely related compounds.

Depending on the circumstances such as the crop wherein fungi are to be combated, the environmental conditions or other factors, a composition of the invention in addition to said fungicidally active compounds of formula I may also contain other active ingredients such as other biocides (e.g. pesticides, including but not limited to insecticides, nematocides, and acaricides; fungicides or herbicides) or plant nutrients or fertilizers.

Examples of other fungicides which can be combined with the active compounds of the invention include especially ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of nonazole EBIs include but are not limited to nuarimol, fenarimol, fenpropimorph, tridemorph and fenpropidine. Other fungicides which can be combined with the enzyme preparation of the invention include anilides, e.g. carboxin, matalaxyl, furalaxyl, ofurace, benalaxyl, mepronil, flutolanil, pencycuron and oxadixyl; benzimidazoles, e.g. benomyl and carbendazim; carbamates, e.g. maneb, mancozeb and propamocarb; dicarboximides, e.g. iprodione, vinclozolin and procymidone; phosphorus derivatives, e.g. pyrazophos, tolclofosmethyl and fosetyl aluminum; and miscellaneous compounds, including iminoctadine, guazatine, dicloran, chlorothalonil, pyrifexox, ethirimol, cymoxanil and anilazine.

For combating fungi in animals including humans the composition of the invention would usually comprise said active compounds of formula I alone with a physiologically compatible carrier or diluent, but it may also be combined with other active ingredients such as an antibioticum.

A fungicidal composition according to the invention having a fungicidally active compound of the invention as its active ingredient may for agronomical and/or horticultural applications be formulated by mixing the active principle with suitable inert and compatible carriers or diluents to obtain a composition of the type generally used in agricultural compositions such as a wettable powder, an emulsifiable concentrate, a concentrated emulsion, a granular formulation, a water soluble powder, an alginate, a zanthan gum and/or an aerosol. As solid carriers bentonite diatomeceous earth, apatite, gypsum, talc, pyrophylite, vermiculite, ground shells, and clay may be mentioned. A surface active agent may also be added with the purpose of producing a homogeneous and stable formulation.

The diluent or carrier in the composition of the invention can as indicated be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9 -tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a dispersible powder, an emulsifiable concentrate or granules. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent.

A dusting powder comprises the active ingredient intimately mixed and ground with a solid pulverulent diluent, for example, kaolin.

A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit.

wettable powders, granules or grains usually comprise the active ingredient in admixture with a suitable surfactant and an inert powder diluent such as china clay.

Another suitable concentrate is a flowable suspension concentrate which is formed by grinding the active ingredient with water or other liquid, a wetting agent and suspending agent.

For use in combating fungi in animals including mammals the active compounds of the invention may be formulated by mixing a compound of formula I or in a specific embodiment, Iawith suitable inert and compatible carriers known in the art for use in topical formulations, or for use as a systemic agent, as applicable.

The concentration of the active compounds of the invention described herein in the compositions of the invention may vary within a wide range depending on the type of formulation and the field of application.

It is contemplated that the active compound of the invention may be applied in concentrations ranging from about, 0.01 µg/ml to about 100 µg/ml for use in controlling fungi in animals.

In its fourth aspect the invention relates to methods of combating fungi in plants or animals including mammals, wherein an effective amount of a fungicidally active compound of formula I or in a specific embodiment, Ia is applied to a region to be treated.

In connection with this aspect the compositions of the invention may for agronomical or horticultural uses be applied to a region to be treated either directly to the soil as a pre-emergence treatment or to the foliage or fruits of the plants as a post-emergence treatment. Depending on the crop and circumstances the treatment may be postponed until seeds or fruits appear on the plants, wherein fungi are to be controlled.

The active preparation or the compositions of the invention can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary.

Sometimes, it is practicable to treat the roots of a plant before or during planting, for example by dipping the roots in a suitable liquid or solid composition. When the active preparation of the invention is applied directly to the plant a suitable rate of application is from about 0.001 to about 10 kg per hectare, preferably from about 0.05 to about 1 kg per hectare.

In the method of the invention the active preparation of the invention alone or in combination with a conventional biocide can also be applied to seeds or habitat. Thus the preparation can be applied directly to the soil before, at or after drilling so that the presence of active ingredient in the soil can control the growth of fungi which my attack seeds.

The compositions may be applied in amounts corresponding to from about 1 g to about 100 kg fungicidally active compound per hectare.

When the soil is treated directly the active preparation alone or in admixture with the conventional biocide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from about 0.01 to about 20 kg per hectare, more preferably from about 0.05 to about 5 kg per hectare.

The concentration of the fungicidally active compounds of the invention in the compositions of the present invention when used alone or in combination with a conventional fungicide, as applied to plants is preferably within the range from about 0.01 to about 3.0 percent by weight, especially from about 0.01 to about 1.0 percent by weight. In a primary composition the amount of active compound can vary widely and can be, for example, in the range from about 5 to about 95 percent by weight of the composition.

The concentration of the other fungicidally active ingredient in the mixed composition of the present invention, as applied to plants is preferably within the range from about 0.001 to about 10 percent by weight, especially from about 0.01 to about 5 percent by weight. In a primary composition the amount of other active ingredient can vary widely and can be, for example, from about 5 to about 80 percent by weight of the composition.

For veterinary and medicinal uses the composition of the invention may be applied to a region to be treated when the diagnosis has been established by the veterinarian or physician.

The compositions of the invention may also be used for the preservation of wood by adding effective amounts of said compositions to wood preservation and/or impregnation compositions.

Also, the compositions of the invention may be useful as a fungicide and preservant in paints both to prevent growth in the paint during storage, and growth on the painted object such as the plastered surface of a house. An amount of said composition(s) effective to prevent the growth of a fungus on the wood is applied to the wood.

Further the compositions of the invention may due to their low toxicity be used for the preservation of edible goods such as jams, marmalade, or other such items where the principle may be added subsequent to any cooking process. An amount of the composition effective to prevent the growth of the fungus in the edible product is applied to the edible product.

Also, the compositions of the invention may be used as a fungicidal additive to growth media for various microorganisms such as E. coli, Pseudomonas aeroginosa, Serpula lacrymans and Cladosporium sp. An amount of composition effective to prevent the growth of fungi is added to the media.

Description of the strain
Colony:
On potato carrot agar greyish sepia to isabelline; reverse sepia.
Mycelium:
Sparse to abundant, composed of yellowish brown to light brown, branched, septate hyphae 2–3.5 µm wide, with chiefly smooth, but sometimes roughened walls.
Conidiomata:
Pycnidial, partially immersed in the agar, solitary, yellowish brown to dark brick, unilocular, subglobose with short necks, 160–180 µm wide, overall height 180–200 µm, ostiolate. Conidiomatal (pycnidial) wall pseudoparenchymatic, composed of 4–7 cell layers (textura angularis); the outer cell layers brown to dark brick, thick-walled, the innermost layer lining the pycnidial cavity yellowish to hyaline.
Ostioles:
Circular 15–20 µm wide, surrounded by cells darker than the pycnidial wall.
Conidiogenous cells:
Hyaline, subglobose to ampulliform, phialidic, with periclinal thickening, arising from the innermost layer of cells lining the pycnidial cavity.
Conidia:
Yellowish brown to pale brown, cylindrical to ellipsoid, apex rounded, base truncate or rounded (6.5–9) µm×(2–3)µm, >93% medianly 1-septate, <7% 2–3 septate.

CMI CC 337158 is a new species in the genus Ascochyta. It belongs to the section Ascochytella. It is closely related to A. zeicola Ellis & Everhart, but differs in having a small percentage of 2–3 septate conidia. With age some pycnidia produce >70% 2–3 septate conidia.

Cultivation of strain
The fungus may be grown on agar slants containing the following ingredients in grams/liter:

| | |
|---|---|
| yeast extract | 4.0 |
| potassium dihydrogen phosphate | 1.0 |
| magnesium sulphate heptahydrate | 0.1 |
| glucose | 15 |
| Bacto ® (Difco Laboratories, Detroit, USA) agar | 20 |

This substrate is autoclaved at 121° C. for 20 or 40 minutes and will, hereinafter, be referred to as YPG agar. Slants contain 12 ml YPG agar and after inoculation they are incubated at 20°–25° C. for 7 days or longer.

Fungicide production
A substrate for shake flasks was prepared using tap water with the following ingredients in grams per liter:

| | |
|---|---|
| maltodextrin-Glucidex ®6 | 90 |
| ammonium sulphate | 1.0 |
| corn steep liquor | 25 |
| potassium dihydrogen phosphate | 0.5 |

The pH is adjusted to 4.5 before the substrate is sterilized at 121° C. for 40 minutes. A 500 ml Erlenmeyer flask with 100 ml of substrate was inoculated with $10^6$ spores from a YPG agar slant previously inoculated with CMI CC 337158. The flasks were shaken at 230 rpm at 25° C. for 3–7 days whereafter the fermentation broth was centrifuged. The supernatant containing the fungicide was thereby separated from the mycelium. The mycelium was discarded and the supernatant was analyzed for fungicidal activity.

The fungicide can also be produced in surface cultures in accordance with well known procedures.

The fermentation can also be carried out in media containing other sources of carbon and nitrogen assimilable by the microorganism and generally low levels of inorganic salts. In addition, the media may be supplemented with trace metals, although if complex sources of carbon and nitrogen are employed, they are usually present in the complex sources.

Temperature and pH stability
The fungicides of formula I are active over a wide range of temperatures and pHs. The stability at pH 3–9 and from 5°–55° C. for compound Ia is shown in the FIG. 1. The experiment was carried out in citrate/phosphate buffer from pH 3–7, and Tris/HCl buffer from 7 to 9. After adjustment of the pH, the samples were allowed to stand at the respective temperatures for 17.5 hours. Then the residual activity was measured, and the values calculated as a percentage of the activity of the zero sample.

FIG. 1 shows the relationship between residual activity and pH for a number of temperatures. From the figure it is seen that the compounds of the invention exhibit good stability at both low and high pH values with a stability minimum around pH 5 to pH 7. Also, FIG. 1 shows that the compounds of the invention exhibits the best stability at low temperatures.

Extraction of the active compound
The compound of formula Ia of this invention could be extracted from the culture broth as follows:

9.65 liters of culture broth were filtered after addition of 80 g High Flow Supercell (filter aid), whereby 5.4 l of filtrate was obtained. The mycelium was then resuspended in 3 l of water, and filtered once more to obtain 3.5 l filtrate.

The filtrate was then filtered on Supra 50 filters from Seitz (Germany). This filtrate was concentrated by vacuum evaporation at 20° C., to 1 liter.

To remove impurities from the concentrate 1000 ml ethanol was added. After mixing for 15 minutes the precipitate was filtered off. The filtrate was then concentrated to 800 ml by vacuum evaporation at 20° C. The pH of this concentrate was adjusted to 3.0 and then 800 ml ethylacetate was added. This mixture was shaken for 5 minutes in a separating funnel and then left for 15 minutes to separate into 2 phases.

The upper phase (ethylacetate) was placed in a deep freezer over night, in order to freeze out the water, which the next day was quickly filtered off on a fiberglass filter GF/F (Whatman). The waterfree filtrate was then concentrated by vacuum evaporation at 20° C. to 100 ml.

The lower phase was extracted once more with one volume of ethylacetate. The ethylacetate phase from this extraction was treated as mentioned above. After concentration it was mixed with the first ethylacetate concentrate, and then further concentrated to 50 ml by vacuum evaporation. The 50 ml concentrate was placed in a separating funnel with 300 ml acetonitrile and was then extracted with 2×500 ml hexane. After extraction 370 ml acetonitrile phase was concentrated to about 100 ml and was then left overnight in the refrigerator to crystallize.

The crystals were isolated and dissolved in a small amount of acetonitrile filtered on a 0.45 μm membrane filter and then placed at room temperature to crystallize for 3–4 hours. The crystals were separated from the mother liquid and dried after rinsing with a small amount of acetonitrile.

The mother liquid was further concentrated and another crystallization was made. This was continued until no further crystallization took place.

The amount of crystals obtained was about 800 mg, corresponding to a recovery of one third of the activity found in the culture broth.

Analysis—HPLC method

Column: Nucleosil $C_{18}$ 4.6×120mm
Flow : 1 ml/min
Eluent: 48% acetonitrile in deionized water+0.05% trifluor acetic acid
Detector: 280 nm
Retention time about 10 minutes Structure determination of
5,5',6,6',7,7'-Hexahydro-1,1',5,5',6,8,8'-heptahydroxy-3,6',10a,10a'-tetramethyl-9,9'-dioxo-[2,2'-bixanthene].

The structure was determined using X-ray crystallography on crystals achieved from recrystallization from acetonitrile. The structure was confirmed by the $^1$H and $^{13}$C NMR and mass spectroscopic determinations.

Crystallographic data.

Unit cell dimensions and reflection intensities were measured on an Enraf-Nonius CAD-4 diffractometer with graphite monochromated MoK γ-radiation. Due to the rather small crystal size data were collected at low temperature. The structure was determined using the SHELX-76 (G. M. Sheldrick. SHELX-76. Program for crystal structure determination. University of Cambridge, England, 1976) and SHELX-86 (G. M: Sheldrick. SHELX-86. Program for crystal structure solution. University of Göttingen, Federal Republic of Germany, 1986) programs.

Figure 2:
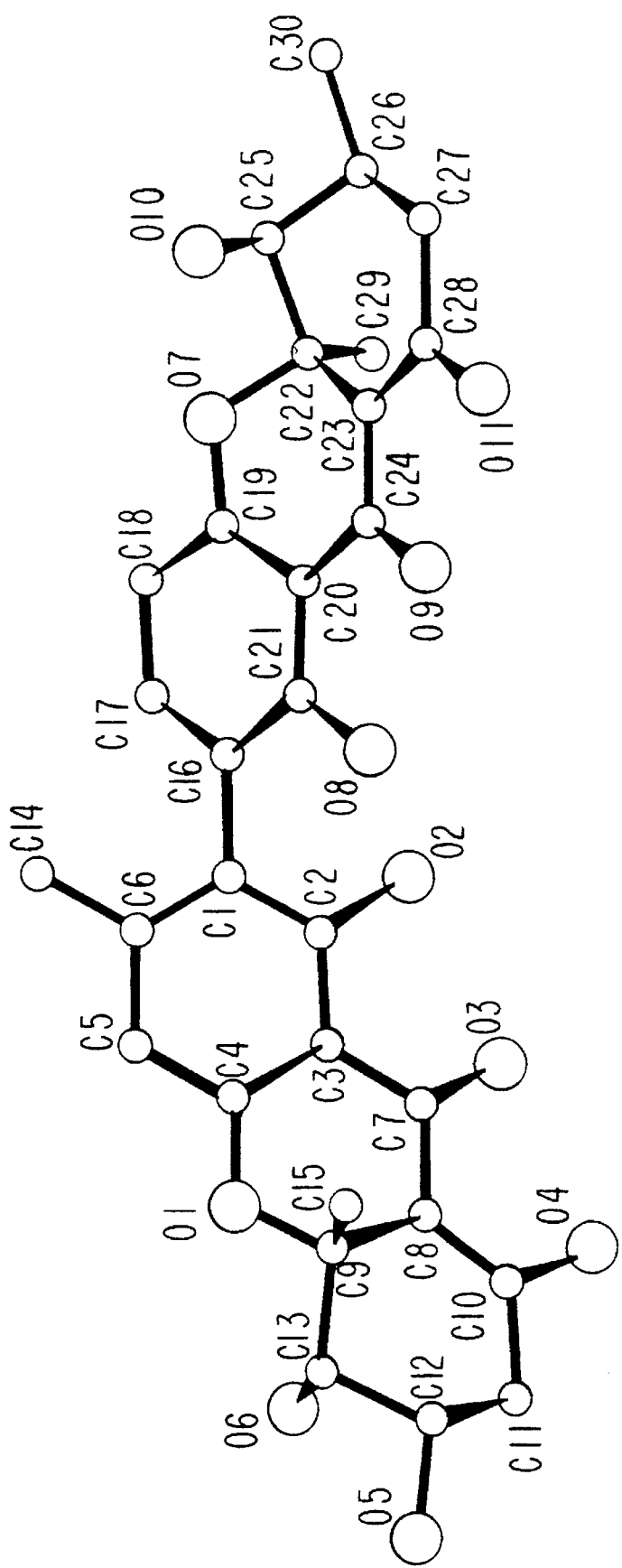
FIG. 2 shows the structure of a compound according to the invention.

A summary of data is given in Table 1, and the resultant atomic coordinates are listed in Table 2. Bond lengths are given in Table 3 and the molecular structure is depicted in FIG. 2.

The number of observed reflections was too low for inclusion of H atoms, and only isotropic thermal parameters were used for C and O atoms.

TABLE 1

| Crystal data and experimental conditions | |
|---|---|
| Molecular formula | $C_{30}H_{30}O_{11}$ |
| $M_r$ | 566.5604 |
| Crystal system | Orthorhombic |
| Space group | $P2_1 2_1 2_1$ |

TABLE 1-continued

| Crystal data and experimental conditions | |
|---|---|
| a | 6.456 (2) Å |
| b | 16.791 (8) Å |
| c | 23.734 (5) Å |
| V | 2572Å$^3$ |
| Z | 4 |
| $D_x$ | 1.457 g · cm$^{-3}$ |
| F(000) | 1184 |
| Temperature | 122K (−151° C.) |
| Crystal size | 0.20 · 0.10 · 0.05 mm |
| Min. h · k · l | 0 · 0 · 0 |
| Max. h · k · l | 7 · 20 · 28 |
| Measured reflections | 2647 |
| Unique, observed refl. | 899 |
| Parameters | 165 |
| R(F) | 0.068 |
| wR(F) | 0.084 |

TABLE 2

Atomic coordinates and istropic thermal parameters

| ATOM | X/A | Y/B | Z/C | Pop. | U |
|---|---|---|---|---|---|
| C1 | −0.0455 | 0.7231 | 0.3877 | 1.0000 | 0.0167 |
| | 0.0030 | 0.0009 | 0.0007 | 0.0000 | 0.0045 |
| C2 | 0.1253 | 0.6785 | 0.3709 | 1.0000 | 0.0118 |
| | 0.0027 | 0.0009 | 0.0006 | 0.0000 | 0.0041 |
| C3 | 0.1729 | 0.6051 | 0.3963 | 1.0000 | 0.0131 |
| | 0.0028 | 0.0009 | 0.0006 | 0.0000 | 0.0041 |
| C4 | 0.0296 | 0.5750 | 0.4368 | 1.0000 | 0.0152 |
| | 0.0031 | 0.0010 | 0.0006 | 0.0000 | 0.0044 |
| C5 | −0.1502 | 0.6149 | 0.4527 | 1.0000 | 0.0110 |
| | 0.0027 | 0.0009 | 0.0006 | 0.0000 | 0.0039 |
| C6 | −0.1791 | 0.6927 | 0.4288 | 1.0000 | 0.0200 |
| | 0.0029 | 0.0010 | 0.0007 | 0.0000 | 0.0045 |
| C7 | 0.3528 | 0.5588 | 0.3817 | 1.0000 | 0.0126 |
| | 0.0028 | 0.0010 | 0.0006 | 0.0000 | 0.0040 |
| C8 | 0.4045 | 0.4924 | 0.4173 | 1.0000 | 0.0107 |
| | 0.0025 | 0.0010 | 0.0006 | 0.0000 | 0.0039 |
| C9 | 0.2793 | 0.4862 | 0.4720 | 1.0000 | 0.0212 |
| | 0.0029 | 0.0010 | 0.0007 | 0.0000 | 0.0046 |
| C10 | 0.5639 | 0.4423 | 0.4073 | 1.0000 | 0.0218 |
| | 0.0030 | 0.0010 | 0.0007 | 0.0000 | 0.0046 |
| C11 | 0.6273 | 0.3726 | 0.4426 | 1.0000 | 0.0207 |
| | 0.0029 | 0.0010 | 0.0007 | 0.0000 | 0.0048 |
| C12 | 0.5178 | 0.3775 | 0.4999 | 1.0000 | 0.0211 |
| | 0.0030 | 0.0010 | 0.0007 | 0.0000 | 0.0047 |
| C13 | 0.2891 | 0.4000 | 0.4950 | 1.0000 | 0.0193 |
| | 0.0030 | 0.0010 | 0.0007 | 0.0000 | 0.0047 |
| C14 | −0.3613 | 0.7385 | 0.4511 | 1.0000 | 0.0142 |
| | 0.0028 | 0.0009 | 0.0006 | 0.0000 | 0.0041 |
| C15 | 0.3573 | 0.5446 | 0.5182 | 1.0000 | 0.0111 |
| | 0.0026 | 0.0009 | 0.0006 | 0.0000 | 0.0040 |
| C16 | −0.0764 | 0.8059 | 0.3668 | 1.0000 | 0.0112 |
| | 0.0027 | 0.0009 | 0.0006 | 0.0000 | 0.0039 |
| C17 | −0.2580 | 0.8304 | 0.3401 | 1.0000 | 0.0166 |
| | 0.0029 | 0.0010 | 0.0007 | 0.0000 | 0.0042 |
| C18 | −0.2948 | 0.9108 | 0.3225 | 1.0000 | 0.0156 |
| | 0.0030 | 0.0010 | 0.0007 | 0.0000 | 0.0042 |
| C19 | −0.1371 | 0.9650 | 0.3306 | 1.0000 | 0.0182 |
| | 0.0029 | 0.0010 | 0.0007 | 0.0000 | 0.0045 |
| C20 | 0.0589 | 0.9434 | 0.3562 | 1.0000 | 0.0117 |
| | 0.0027 | 0.0010 | 0.0006 | 0.0000 | 0.0040 |
| C21 | 0.0779 | 0.8638 | 0.3746 | 1.0000 | 0.0199 |
| | 0.0031 | 0.0010 | 0.0007 | 0.0000 | 0.0045 |
| C22 | 0.0007 | 1.0944 | 0.3028 | 1.0000 | 0.0195 |
| | 0.0028 | 0.0010 | 0.0007 | 0.0000 | 0.0046 |
| C23 | 0.1784 | 1.0822 | 0.3446 | 1.0000 | 0.0105 |
| | 0.0029 | 0.0009 | 0.0006 | 0.0000 | 0.0040 |
| C24 | 0.2059 | 1.0036 | 0.3681 | 1.0000 | 0.0197 |
| | 0.0028 | 0.0011 | 0.0007 | 0.0000 | 0.0042 |
| C25 | −0.0823 | 1.1806 | 0.3070 | 1.0000 | 0.0214 |
| | 0.0030 | 0.0010 | 0.0007 | 0.0000 | 0.0044 |
| C26 | 0.0928 | 1.2378 | 0.2953 | 1.0000 | 0.0263 |

TABLE 2-continued

Atomic coordinates and istropic thermal parameters

| ATOM | X/A | Y/B | Z/C | Pop. | U |
|---|---|---|---|---|---|
|  | 0.0031 | 0.0010 | 0.0007 | 0.0000 | 0.0051 |
| C27 | 0.2772 | 1.2286 | 0.3393 | 1.0000 | 0.0222 |
|  | 0.0030 | 0.0010 | 0.0007 | 0.0000 | 0.0046 |
| C28 | 0.3057 | 1.1423 | 0.3588 | 1.0000 | 0.0127 |
|  | 0.0029 | 0.0009 | 0.0007 | 0.0000 | 0.0041 |
| C29 | 0.0648 | 1.0695 | 0.2431 | 1.0000 | 0.0172 |
|  | 0.0030 | 0.0010 | 0.0007 | 0.0000 | 0.0045 |
| C30 | 0.0195 | 1.3230 | 0.2975 | 1.0000 | 0.0270 |
|  | 0.0031 | 0.0011 | 0.0007 | 0.0000 | 0.0050 |
| O1 | 0.0619 | 0.5028 | 0.4613 | 1.0000 | 0.0118 |
|  | 0.0017 | 0.0006 | 0.0004 | 0.0000 | 0.0027 |
| O2 | 0.2515 | 0.7062 | 0.3294 | 1.0000 | 0.0224 |
|  | 0.0019 | 0.0007 | 0.0004 | 0.0000 | 0.0031 |
| O3 | 0.4597 | 0.5757 | 0.3394 | 1.0000 | 0.0180 |
|  | 0.0019 | 0.0006 | 0.0004 | 0.0000 | 0.0029 |
| O4 | 0.6806 | 0.4527 | 0.3611 | 1.0000 | 0.0254 |
|  | 0.0020 | 0.0007 | 0.0005 | 0.0000 | 0.0030 |
| O5 | 0.5233 | 0.2963 | 0.5242 | 1.0000 | 0.0249 |
|  | 0.0019 | 0.0007 | 0.0004 | 0.0000 | 0.0032 |
| O6 | 0.1830 | 0.3493 | 0.4571 | 1.0000 | 0.0195 |
|  | 0.0019 | 0.0006 | 0.0004 | 0.0000 | 0.0029 |
| O7 | −0.1763 | 1.0430 | 0.3190 | 1.0000 | 0.0206 |
|  | 0.0019 | 0.0007 | 0.0004 | 0.0000 | 0.0029 |
| O8 | 0.2561 | 0.8428 | 0.4039 | 1.0000 | 0.0214 |
|  | 0.0020 | 0.0007 | 0.0005 | 0.0000 | 0.0030 |
| O9 | 0.3612 | 0.9905 | 0.4011 | 1.0000 | 0.0212 |
|  | 0.0018 | 0.0007 | 0.0004 | 0.0000 | 0.0030 |
| O10 | 0.4639 | 1.1313 | 0.3934 | 1.0000 | 0.0242 |
|  | 0.0020 | 0.0007 | 0.0005 | 0.0000 | 0.0032 |
| O11 | −0.1528 | 1.1941 | 0.3640 | 1.0000 | 0.0202 |
|  | 0.0019 | 0.0006 | 0.0004 | 0.0000 | 0.0030 |

TABLE 3

Bond lengths and angles

| C2—C1 | 1.391 | (0.023) |
|---|---|---|
| C6—C1 | 1.399 | (0.023) |
| C6—C1—C2 | 119.5 | (1.4) |
| C16—C1 | 1.489 | (0.022) |
| C16—C1—C2 | 120.8 | (1.6) |
| C15—C1—C6 | 119.4 | (1.6) |
| C3—C2 | 1.407 | (0.021) |
| C3—C2—C1 | 121.4 | (1.5) |
| O2—C2 | 1.360 | (0.018) |
| O2—C2—C1 | 120.0 | (1.4) |
| O2—C2—C3 | 118.7 | (1.5) |
| C4—C3 | 1.426 | (0.024) |
| C4—C3—C2 | 117.2 | (1.6) |
| C7—C3 | 1.440 | (0.023) |
| C7—C3—C2 | 123.0 | (1.5) |
| C7—C3—C4 | 119.7 | (1.4) |
| C5—C4 | 1.392 | (0.023) |
| C5—C4—C3 | 123.6 | (1.5) |
| O1—C4 | 1.361 | (0.018) |
| O1—C4—C3 | 120.2 | (1.6) |
| O1—C4—C5 | 116.2 | (1.5) |
| C6—C5 | 1.435 | (0.022) |
| C6—C5—C4 | 116.0 | (1.5) |
| C5—C6—C1 | 121.8 | (1.6) |
| C14—C6 | 1.502 | (0.023) |
| C14—C6—C1 | 122.8 | (1.5) |
| C14—C6—C5 | 115.4 | (1.5) |
| C8—C7 | 1.439 | (0.021) |
| C8—C7—C3 | 117.6 | (1.5) |
| O3—C7 | 1.249 | (0.018) |
| O3—C7—C3 | 121.1 | (1.5) |
| O3—C7—C8 | 121.3 | (1.6) |
| C9—C8 | 1.532 | (0.022) |
| C9—C8—C7 | 115.3 | (1.5) |
| C10—C8 | 1.351 | (0.022) |
| C10—C8—C7 | 123.8 | (1.5) |
| C10—C8—C9 | 120.6 | (1.5) |

TABLE 3-continued

Bond lengths and angles

| C13—C9 | 1.549 | (0.022) |
|---|---|---|
| C13—C9—C8 | 109.9 | (1.4) |
| C15—C9 | 1.555 | (0.021) |
| C15—C9—C8 | 112.6 | (1.4) |
| C15—C9—C13 | 109.1 | (1.3) |
| O1—C9 | 1.453 | (0.021) |
| O1—C9—C8 | 110.4 | (1.3) |
| O1—C9—C13 | 106.3 | (1.4) |
| O1—C9—C15 | 108.4 | (1.3) |
| C11—C10 | 1.495 | (0.023) |
| C11—C10—C8 | 126.7 | (1.6) |
| O4—C10 | 1.343 | (0.019) |
| O4—C10—C | 119.3 | (1.5) |
| O4—C10—C | 114.0 | (1.6) |
| C12—C11 | 1.536 | (0.025) |
| C12—C11—C10 | 109.2 | (1.5) |
| C13—C12 | 1.529 | (0.026) |
| C13—C12—C11 | 112.9 | (1.4) |
| O5—C12 | 1.480 | (0.02) |
| O5—C12—C11 | 106.6 | (1.4) |
| O5—C12—C13 | 106.3 | (1.4) |
| C12—C13—C9 | 107.3 | (1.5) |
| O6—C13 | 1.415 | (0.019) |
| O6—C13—C9 | 108.5 | (1.3) |
| O6—C13—C12 | 111.6 | (1.4) |
| C17—C16 | 1.395 | (0.023) |
| C17—C16—C1 | 122.7 | (1.6) |
| C21—C16 | 1.405 | (0.022) |
| C21—C16—C1 | 120.5 | (1.6) |
| C21—C16—C16 | 116.8 | (1.5) |
| C18—C17 | 1.433 | (0.022) |
| C18—C17—C16 | 123.4 | (1.7) |
| C19—C18 | 1.379 | (0.024) |
| C19—C18—C17 | 117.3 | (1.7) |
| C20—C19 | 1.449 | (0.023) |
| C20—C19—C18 | 122.5 | (1.5) |
| O7—C19 | 1.362 | (0.018) |
| O7—C19—C18 | 118.0 | (1.6) |
| O7—C19—C20 | 119.2 | (1.5) |
| C21—C20 | 1.412 | (0.022) |
| C21—C20—C19 | 116.3 | (1.6) |
| C24—C20 | 1.414 | (0.023) |
| C24—C20—C19 | 119.4 | (1.5) |
| C24—C20—C21 | 123.8 | (1.6) |
| C20—C21—C16 | 123.6 | (1.7) |
| O8—C21 | 1.389 | (0.021) |
| O8—C21—C16 | 118.5 | (1.4) |
| O8—C21—C20 | 117.9 | (1.6) |
| C23—C22 | 1.531 | (0.023) |
| C25—C22 | 1.546 | (0.022) |
| C25—C22—C23 | 110.1 | (1.3) |
| C29—C2 | 1.535 | (0.023) |
| C29—C22—C23 | 111.1 | (1.4) |
| C29—C22—C25 | 114.1 | (1.3) |
| O7—C22 | 1.482 | (0.020) |
| O7—C22—C23 | 109.4 | (1.2) |
| O7—C22—C25 | 105.1 | (1.3) |
| O7—C22—C29 | 106.7 | (1.3) |
| C24—C223 | 1.444 | (0.022) |
| C24—C23—C22 | 117.6 | (1.5) |
| C28—C23 | 1.343 | (0.021) |
| C28—C23—C22 | 121.4 | (1.4) |
| C28—C23—C24 | 121.0 | (1.5) |
| C23—C24—C20 | 119.6 | (1.6) |
| O9—C24 | 1.291 | (0.019) |
| O9—C24—C20 | 121.4 | (1.5) |
| O9—C24—C23 | 119.0 | (1.6) |
| C26—C25 | 1.509 | (0.024) |
| C26—C25—C22 | 108.9 | (1.5) |
| O11—C25 | 1.446 | (0.018) |
| O11—C25—C22 | 108.4 | (1.3) |
| O11—C25—C26 | 107.9 | (1.4) |
| C27—C26 | 1.591 | (0.034) |
| C27—C26—C25 | 112.3 | (1.4) |
| C30—C26 | 1.508 | (0.024) |
| C30—C26—C25 | 111.3 | (1.6) |
| C30—C26—C27 | 107.7 | (1.5) |

TABLE 3-continued

Bond lengths and angles

| | | |
|---|---|---|
| C28—C27 | 1.533 | (0.021) |
| C28—C27—C26 | 112.3 | (1.5) |
| C27—C28—C23 | 124.1 | (1.6) |
| O10—C28 | 1.323 | (0.020) |
| O10—C28—C23 | 121.5 | (1.4) |
| O10—C28—C27 | 114.3 | (1.5) |
| C9—O1—C4 | 113.2 | (1.3) |
| C22—O7—C19 | 118.0 | (1.4) |

NMR-Spectroscopy $^1$H NMR and $^{13}$C NMR spectra for the isolate were established in relation to tetramethylsilane (TMS) by dissolving the crystals in tetrahydrofuran$_8$ (THF-d$_8$) and using a Bruker WM 400 instrument at magnetic field strengths of 400 MHz and 100.6 MHz, respectively.

The spectra are listed below:

$^1$H-NMR, 400 MHz (THF-d$_8$) δ: 1.15 (d, 3H), 1.45 (s, 3H), 1.5 (s, 3H), 2.05 (s, 3H) 2.2 (m, 1H), 2.3 (dd, 1H), 2.45 (dd, 1H), 2.55 (dd, 1H), 2.7 (dd, 1H), 3.75 (s, 1H), 3.95 (s, 1H), 4.0 (m, 1H), 4.1 (s, 1H), 4.3 (s, 1H), 4.7 (s, 1H), 6.3 (s, 1H), 6.45 (d, 1H), 7.2 (d, 1H), 11.7 (s, 1H), 11.85 (s, 1H), 13.75 (s, 1H), 13.85 (s, 1H).

$^{13}$C-NMR, 100.6 MHz (THF-d$_8$) δ: 18.3, 21.2, 25.9, 26.2, 29.9, 33.8, 35.6, 65.9, 75.2, 75.9, 82.1, 83.2, 105.3, 105.4, 105.5, 107.5, 108.5, 109.8, 117.5, 118.7, 141.2, 150.0, 158.4, 159.3, 160.9, 161.1, 176.0, 178.4, 188.8, 189.3.

Mass spectroscopy

Electron impact (EI) mass spectrum was performed at 70 eV on a VG 70–250 SQ spectrometer with direct insertion via an insertion probe heated from 30° C. to 300° C. in 100° C./min. The scanning speed was 10 s/decade in the range 80 to 800 Dalton, and the resolution was 3300.

Exact mass:

| | |
|---|---|
| measured | 566.1786 |
| calculated for $C_{30}H_{30}O_{11}$ | 566.1788. |
| MS m/z (%): | 566 (100), 548 (35), 530 (22), 500 (42), 472 (25), 407 (17). |

Bioassay $10^6$ spores of Botrytis cinerea were added to 50 ml of dilute salts comprising:

| | |
|---|---|
| ammonium hydrogen phosphate | 66 mg |
| potassium dihydrogen phosphate | 68 mg |
| dipotassium hydrogen phosphate | 87 mg |
| calcium chloride-2-hydrate | 7.4 mg |
| magnesium chloride-6-hydrate | 10 mg | made up to 1 liter with distilled water and sterilized at 121° C. for 20 minutes.

This was mixed with 50 ml YPG agar at a temperature which favored the viability of Botrytis spores suitably in the temperature range from about 30° C. to about 45° C. where the agar is kept fluid without any harm to the spores. 12 ml of this mixture were poured into 9 cm petri dishes and allowed to solidify. 1–5 holes of 4 mm diameter were punched in the agar and 15 μl culture broth was put in each hole.

The petri dishes were incubated at 20°–25° C. for 2 days. The presence of a fungicide will reveal itself as a clear nongrowth zone around the holes—the larger the zone the stronger the fungicide. The supernatant under these conditions produced a clear zone of 20 mm. This was already visible after 1 day.

Mammalian pathogenicity

Culture broth containing the fungicide and viable spores and mycelium showed no effect on mice, intraperitoneally applied at the rate of 20 ml per kg body weight. The broth contained approximately $1\times10^7$ viable counts/ml.

Fungicidal activity

The partially purified broth containing 35 μg/ml of the compound of formula Ia of the invention, has been found to have an inhibitory effect on the growth of fungi belonging to the following classes:

| | |
|---|---|
| Class Oomycetes, | genus Pythium, e.g. P. ultimum, |
| | genus Phytophthora, e.g. P. infestans |
| Class Zygomycetes, | genus Rhizomucor, e.g. R. pusillus |
| Class Ascomycetes, | genus Erysiphe, e.g. E. graminis |
| | genus Saccharomyces, e.g. S. cerevisiae |
| | form-genus Aspergillus, e.g. |
| | A. fumigatus, A. niger |
| | form-genus Penicillium, e.g. P. digitatum |
| Class Deuteromycetes, | genus Fusarium, e.g. F. oxysporum |
| | genus Botrytis, e.g. B. cinerea |
| | genus Cercospora, e.g. C. beticola |
| | genus Candida, e.g. C. albicans |
| Class Basidomycetes, | genus Coniophora, e.g. C. puteana |
| | genus Gloeophyllum, e.g. G. trabeum |
| | genus Poria, e.g. P. placenta |

Of these fungi Aspergillus fumigatus, Rhizomucor pusillus causing mucormycosis, and Candida albicans causing candidiasis, onychomycosis, tinea corporis, tinea pedis, vaginitis, and thrush, are generally regarded as human pathogens, and especially Aspergillus fumigatus causes aspergillosis in humans and other mammals, and birds. Whereas Coniophora puteana, Gloeophyllum trabeum, and Poria placenta all are wood destroying fungi.

The remaining fungi in the list are all regarded as plant pathogens.

Bacterial activity

The partially purified broth containing 35 μg/ml of the compound of formula Ia of the invention, has been found to have an inhibitory effect on the growth of bacteria belonging to the following orders:

Order Eubacteriales, family Bacillaceae, genus Bacillus,
    e.g. B. cereus, B. subtills family Enterobacteriaceae, genus Erwinia,
    e.g. Erwinia sp.

The inhibitory effect of the culture broth is not very strong against Staphylococcus aureus.

At 35 μg/ml the culture broth does not seem to inhibit the growth of Pseudomonas aeroginosa, Escherichia coli, Serpula lacrymans and Cladosporium herbarium.

Biological activity on plants

At the concentrations used in the following examples no phytotoxic activity has been observed.

EXAMPLES

Example 1

Activity against Botrytis cinerea on tomato plants

Tomato plants (variety "First in Field", 5 weeks old) were treated with a liquid suspension containing 0.1 mg active ingredient per ml. The plants were kept 24 hours in a green house to dry before they were inoculated with a spore suspension containing about $10^5$ spores per ml in 25% grapefruit juice. The plants were then incubated for 6 days (16 hours light (1000 lux) and 8 hours dark at 15° C. to 20°

C.) in clear polyethylene bags to raise the relative humidity to 95% to 100%. No attack from the fungus was observed. Control plants that were treated as above except for the application of the active ingredient in suspension were all overgrown with *Botrytis cinerea*.

Example 2

Activity against *Erysiphe graminis* on barley plants

Barley plants (variety "Catin Carlsberg", 1 week old) were treated with culture broth containing 0.01–1.0 mg active ingredient per ml. The plants were kept for 24 hours in a green house to dry before they were inoculated by shaking diseased plants over them. The density of spores were about 100 spores per $mm^2$. The plants were then incubated for 8 days (16 hours light (5000–6000 lux) and 8 hours dark at 18° C. to 23° C. No attack from the fungus was observed, while control plants that were treated as above except for the application of the active ingredient were all heavily infected.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for combating a fungus infestation at a locus infested with the fungus, comprising applying to the locus a composition comprising (a) a compound having the formula

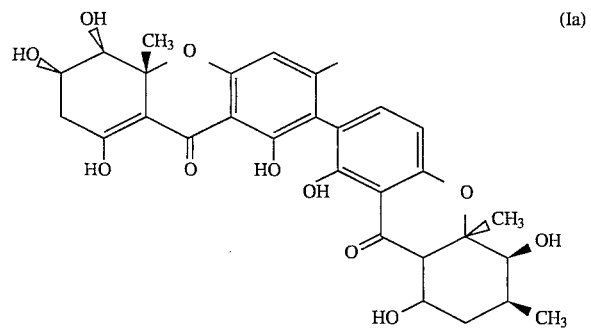

(Ia)

and (b) an inert carrier in an amount effective to prevent the growth of the fungus at the infested locus.

2. The method according to claim 1 in which the compound is present in the amount of from about 0.01 to about 3.0 percent by weight.

3. The method according to claim 1 in which the fungus is selected from the group consisting of Pythium, Phytophthora, Rhizomucor, Erysiphe, Saccharomyces, Aspergillus, Penicillium, Fusarium, Botrytis, Cercospora, Candida, Coniophora, Gloeophylum, and Poria.

4. The method according to claim 1 in which said method combats the infestation of fungus selected from the group consisting of *Erysiphe graminis* and *Phytophthora infestans*.

5. A method for combating a fungus infestation at a locus infested with the fungus, comprising applying to the locus a composition comprising (a) a first active agent having the formula

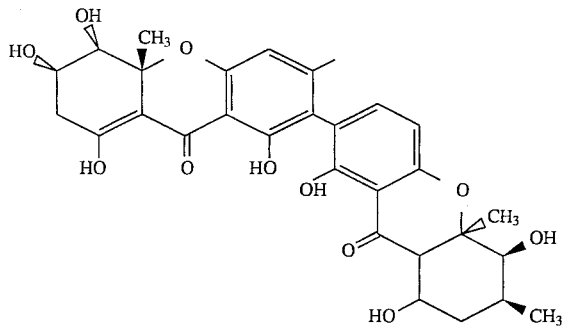

and (b) a second active agent, which second active agent is selected from the group consisting of a biocide, a plant nutrient and a plant fertilizer in an amount effective to prevent the growth of the fungus at the infested locus.

6. The method according to claim 5 in which the biocide is selected from the group consisting of a pesticide, an herbicide, and a fungicide.

7. The method according to claim 6 in which the pesticide is selected from the group consisting of an insecticide, a nematocide, and an acaricide.

8. The method according to claim 6 in which the fungicide is selected from the group consisting of an ergosterol biosynthesis inhibitor, an anilide, a benzimidazole, a carbamate, a dicarboximide, a phosphorous derivative.

9. The method according to claim 5 in which the first active agent is present in the amount of from about 0.01 to about 3.0 percent by weight.

10. The method according to claim 5 in which the second active agent is present in the amount of from about 0.01 to about 10.0 percent by weight.

11. The method according to claim 5 in which the fungus is selected from the group consisting of Pythium, Phytophthora, Rhizomucor, Erysiphe, Saccharomyces, Aspergillus, Penicillin, Fusarium, Botrytis, Cercospera, Candida, Coniophora, Gloeophylum, and Poria.

12. The method according to claim 5 in which said method combats the infestation of fungus selected from the group consisting of *Erysiphe graminis* and *Phytophthora infestans*.

13. A method for combating a fungus infestation in an animal infested with the fungus, comprising administering to the animal a composition comprising (a) an active agent having the formula

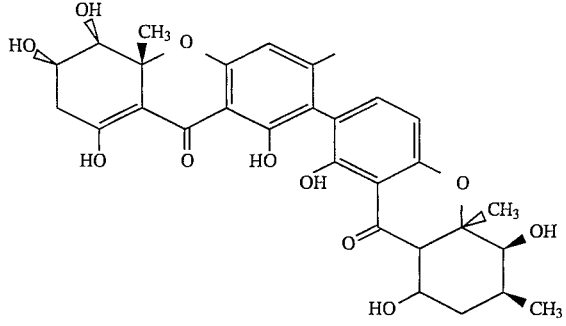

and (b) an inert carrier in an amount effective to prevent the growth of the fungus in said animal.

14. The method according to claim 13, in which the first active agent is present in a concentration from about 0.01 μg/ml to 100 μg/ml.

15. A method for preserving wood comprising applying to the wood a composition comprising (a) a compound having the formula

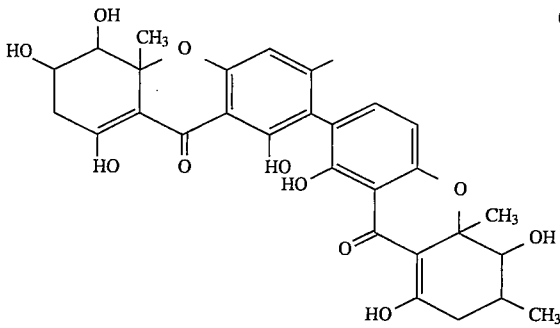

(Ia)

and (b) an inert carrier in an amount effective to prevent the growth of a fungus on the wood.

16. A method for preserving wood comprising applying to the wood a composition comprising (a) a first active agent having the formula

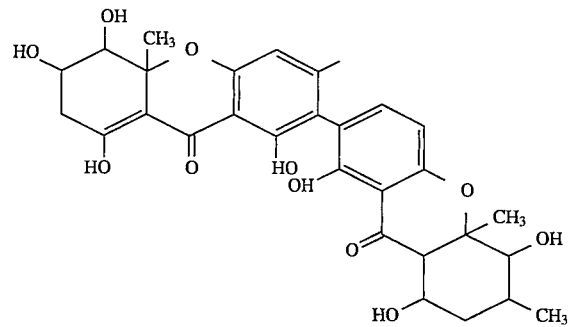

and (b) a second active agent, which second active agent is selected from the group consisting of a biocide in an amount effective to prevent the growth of a fungus on the wood.

17. A method for preserving paint comprising applying to the paint a composition comprising (a) a first active agent having the formula

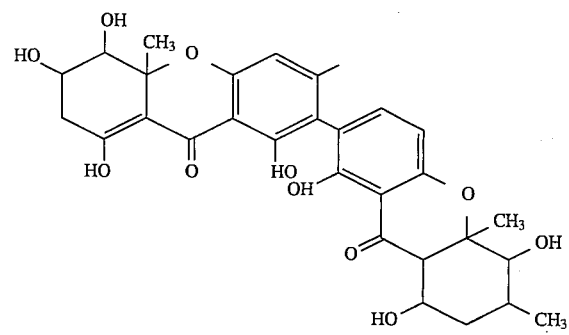

and (b) an inert carrier in an amount effective to prevent the growth of a fungus in the paint.

18. A method for preventing the growth of fungi in media used to culture a microorganism comprising adding to the media a composition comprising (a) a compound having the formula

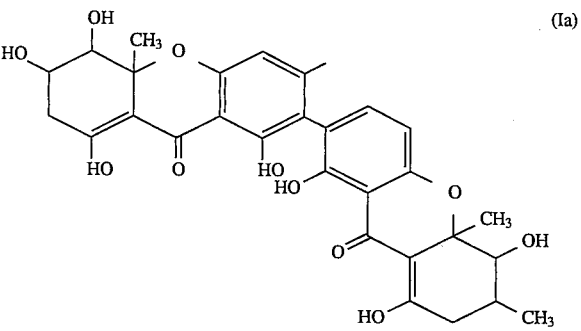

(Ia)

and (b) an inert carrier in an amount to prevent the growth of a fungus in the media used to culture a microorganism.

* * * * *